United States Patent [19]
Dodman

[11] Patent Number: 5,554,383
[45] Date of Patent: Sep. 10, 1996

[54] VETERINARY METHOD FOR CLINICALLY MODIFYING THE BEHAVIOR OF DOGS EXHIBITING CANINE AFFECTIVE AGGRESSION

[75] Inventor: Nicholas H. Dodman, Grafton, Mass.

[73] Assignee: Trustees of Tufts College, Medford, Mass.

[21] Appl. No.: 417,747

[22] Filed: Apr. 6, 1995

[51] Int. Cl.[6] .......................... A61F 2/02; A61K 9/127; A61K 9/20; A61K 31/44
[52] U.S. Cl. .................. 424/451; 424/423; 424/427; 424/430; 424/434; 424/450; 424/464; 424/489; 514/288; 514/315; 514/415
[58] Field of Search .................... 514/288, 315, 514/415; 424/423, 427, 430, 434, 450, 451, 464, 484

[56] References Cited

U.S. PATENT DOCUMENTS 4,704,394  11/1987  Geho ........................... 514/288

OTHER PUBLICATIONS

Fuller, R. W., *J. Clin. Psychiat.* 53(10 Supp.):36–45 (1992);.
*Veterinary Pharmacology and Therapeutics*, 6th Ed., (Booth & McDonald, eds.), Chap. 1, p.7;.
Beaver, B. V., *Appl. Anim. Ethol.* 10:35–43 (1983); and *The Friskies Symposium On Behavior*, Apr. 17, 1994.

*Primary Examiner*—Carlos Azpuru
*Attorney, Agent, or Firm*—David Prashker

[57] ABSTRACT

A veterinary method for clinically modifying the behavior of a household pet dog exhibiting a recognized type of canine affective aggression behavior is provided. The veterinary behavior modification method administers at least one selective serotonin reuptake inhibitor compound to the dog upon one or multiple occasions; and the administration of these compounds will modify clinically the canine affective aggression behavior of the household dog permanently or for an indefinite period of time. This veterinary behavior modification method can be usefully employed as an adjunct to conditioning approaches presently employed and will avoid the need for euthanasia in extreme behavioral circumstances.

7 Claims, 6 Drawing Sheets

WEEK 1 = SACCHARIN CONTROL
WEEK 2-5 = TREATMENT WITH FLUOXETINE

PLEASE CHECK THE APPROPRIATE BOX IF YOUR DOG EXHIBITS ANY OF THE LISTED BEHAVIORS AT ANY TIME WHEN YOU OR ANY MEMBER OF THE FAMILY DO THE FOLLOWING:

| | GROWL | LIFT LIP | SNAP | BITE | NO AGGRESIVE RESPONSE | TRIED |
|---|---|---|---|---|---|---|
| TOUCH DOG'S FOOD WHILE EATING | | | | | | |
| WALK PAST DOG WHILE EATING | | | | | | |
| ADD FOOD WHILE DOG IS EATING | | | | | | |
| TAKE AWAY REAL BONE OR RAWHIDE | | | | | | |
| WALK BY DOG WHEN S/HE HAS A REAL BONE/RAWHIDE | | | | | | |
| TOUCH DELICIOUS FOOD WHEN DOG IS EATING | | | | | | |
| TAKE AWAY A STOLEN OBJECT | | | | | | |
| PHYSICALLY WAKE DOG UP | | | | | | |
| PHYSICALLY DISTURB DOG | | | | | | |
| RESTRAIN DOG WHEN IT WANTS TO GO SOMEPLACE | | | | | | |
| LIFT DOG | | | | | | |
| PET DOG | | | | | | |
| MEDICATE DOG | | | | | | |
| HANDLE DOG'S FACE/MOUTH | | | | | | |
| HANDLE DOG'S FEET | | | | | | |
| TRIM THE DOG'S TOENAILS | | | | | | |
| GROOM DOG | | | | | | |
| BATHE OR TOWEL OFF | | | | | | |
| TAKE OFF OR PUT ON COLLAR | | | | | | |
| PULL DOG BACK BY THE COLLAR OR SCRUFF | | | | | | |
| REACH FOR GRAB DOG BY THE COLLAR | | | | | | |
| HOLD DOG BY THE MUZZLE | | | | | | |
| STARE AT THE DOG | | | | | | |
| REPRIMAND DOG IN LOUD VOICE | | | | | | |
| VISUALLY THREATEN DOG: NEWSPAPER OR HAND | | | | | | |
| HIT THE DOG | | | | | | |
| WALK BY DOG IN CRATE | | | | | | |
| WALK BY/ TALK DOG ON FURNITURE | | | | | | |
| REMOVE DOG FROM FURNITURE PHYSICALY OR VERBALLY | | | | | | |
| MAKE DOG RESPOND TO COMMAND | | | | | | |

FIG. 1

* THE WILCOXON MATCHED PAIRS TEST SHOWS SIGNIFICANT DIFFERENCE ONLY BETWEEN WEEK 1 (CONTROL) AND WEEK 4 MATCHED (P=0.018) AND BETWEEN WEEK 1 AND WEEK 5 (P=0.028).

THE WILCOXON MATCHED-PAIRS TEST SHOWS NO SIGNIFICANT DIFFERENCE BETWEEN WEEK 1 AND ANY OTHER WEEK (P>0.1)

WEEK 1 = SACCHARIN CONTROL
WEEK 2-5 = TREATMENT WITH FLUOXETINE

VETERINARY METHOD FOR CLINICALLY MODIFYING THE BEHAVIOR OF DOGS EXHIBITING CANINE AFFECTIVE AGGRESSION

FIELD OF THE INVENTION

The present invention is concerned generally with the veterinary treatment of animal behavioral problems commonly found in human family households; and is particularly directed to the veterinary clinical modification of affective aggression behaviors expressed by domesticated dogs kept as household pets.

BACKGROUND OF THE INVENTION

Clinical modification of undesirable animal behaviors exhibited by household domesticated pets using psychopharmacological agents is a relatively new phenomenon in veterinary medicine and today is a most-poorly understood therapy among practicing veterinarians. Prior to about 1974, the veterinary science of modifying specific animal behaviors was in its most rudimentary stages; and the idea of pharmacologically treating specific behavior problems in domesticated animals or household pets was in its infancy. Subsequently, between about 1974–1984, such animal behavior modification methods as existed focused primarily upon behavioral shaping techniques developed from the science of ethology, the study of innate animal behavior patterns; and employed conditioning strategies to elicit behavior modifications in the animal. Thus, the use of pharmacologically active substances to control or modify undesired animal behaviors was only just being explored in the mid-1980s as a most radical and suspect approach by practicing veterinarians. Moreover, after 1985 and continuing even to date for most veterinarians, the idea of administering psychopharmacological agents to household pets as a means for clinically modifying undesirable animal behaviors was and remains directly comparable and analogous to the skepticism of clinicians and attending physicians of about 1950 who found the concept of treating humans exhibiting behavioral disorders with psychopharmacological drugs to be a rash and unwholesome idea.

Within this analogous historical context, therefore, it is most valuable to review summarily the nature of human aggression behaviors, their underlying psychological mental disorders, and the development of psychopharmacological methods for controlling acts of human aggression. Human acts performed with the deliberate intent of causing physical harm to persons or property are, by definition, human aggression and have a wide range of causative factors. Moreover, human aggression behaviors and human acts of violence are considered symptoms rather than diseases and are most frequently associated with an underlying psychological disorder rather than a medical condition. Thus depression, schizophrenia, personality disorders, mania, paranoia, temporal lobe dysfunction, and the consequences of substance abuse each may be the underlying disorder associated with one or more specific acts of human aggression. [*Current Medical Diagnosis & Treatment* 1995 Tierney, McPhee and Papadakis, editors, Appleton & Lange, Norwalk, Conn.; Maxmen, J. S. and N. G. Ward, *Essential Psychopathology And Its Treatment*, Second edition, W. W. Norton & Co., 1995.]

It is also noteworthy that human psychopharmacology as a science and the continuing search for the origins and mediators of human aggression behaviors in its many different forms and varieties have been related areas of investigation since the late 1940s. Clinical concerns with treating highly aggressive human individuals were initially and remain today a starting point for inquiries into the range of neurobiological mechanisms that cause, mediate, or control human aggressive behavior patterns; and, within the clinical setting, human aggression is seen as an abnormality, a psychopathological or sociopathological behavior pattern that requires therapeutic treatment.

Human psychopharmacology and human neuropharmacology in particular have evolved and developed in major part as a response to the ongoing need for a range of different agents which can be used in the treatment of diverse pathological aggressive behaviors or for controlling the differing symptoms of aggression and hostility that are part of the human pathological behavioral disorders. A host of human affective mental disorders (including mood disorders such as major depression and bipolar mania and psychotic disorders such as schizophrenia) often include violent behaviors and aggressive outbursts which may be treatable using particular classes of psychopharmacological drugs. In comparison, pathological aggressive behavioral acts based upon neural mechanisms or the intense aggressive behavior exhibited in the course of human addiction to and withdrawal from narcotics-each may require very different classes of psychopharmaceutical agents as therapeutic treatments [Yudofsky et. al., *Psychiatric Annals* 17:397–407 (1987)].

Many different forms of human aggressive behavior are individually known and well characterized either by reports of personal case medical histories or by human experimental-psychological group studies. Due to ethical considerations, however, humans are not suitable candidates for clinical or research experimentation. For these reasons, experimental procedures and settings were designed during the 1960s and 1970s for the purpose of generating a range and variety of animal models which might be representative and illustrative of specific types or selected examples of human aggressive behaviors and/or serve as an indicator for the underlying root causes and mediators of human aggressive behaviors. Thus, almost every major class of psychopharmacological drugs intended for human usage has been investigated in different animal models, each representative of a specified type of human aggressive behavior. These models were conducted mainly in isolated mice and rats that were exposed to pain or other stimuli, but also utilized fish, pigeons, cats and primates as representative subjects. [See for example: Sheard, M. H., "Animal Models Of Aggressive Behavior" in *Animal Models In Psychiatry And Neurology,* Pergamon Press, Oxford, 1977, pp. 247–257; Eichelman, B., "Animal models: Their role in the aggressive behavior of humans", *Progr.. Neuro-Psychopharmacol.* 2:633–643 (1978); and Miczek, K. A., "The Psychopharmacology Of Aggression" in *HANDBOOK OF PSYCHOPHARMACOLOGY,* Vol. 19, Plenum Publishing Corp., 1987, Chap. 4, pp. 183–328 and the references cited therein.]

A summary review of the various types or categories of different animal models often used as representative examples of human aggression behaviors provides insight and understanding as to their intrinsic limitations and substantive restrictions. One animal model experimental design employs exposure to aversive living conditions to engender aggressive behavior. In these model experiments, deprivation of social contact, or crowding and restricted access to limited resources such as food, or the presentation of aversive external stimuli such as electric shock pulses and omission or intermittency of scheduled reinforcement—are used as artificial and experimental manipulations to intentionally induce and elicit aggressive behaviors in the test animals. All of these are environmental manipulations and are usually performed upon placid and domesticated laboratory animals which rarely, if ever, exhibit aggressive behavior. Thus, in this animal model system, to evoke or induce an act of aggression by intentionally exposing an otherwise non aggressive animal subject to aversive environmental stimuli has led to the often expressed view that aggressive behavior represents an antisocial response. [See for example: Malick, J. B., *Curr. Der. Psychopharmacol.* 5:1–27 ( 1979); Oliver et. al., *Psychopharmacoloqy* 97:154–156 (1989); Krsiak, M., Res. Commun. Chem. Path. Pharmacol. 7:253–257 (1974); Oliver, B. and D. von Dalen, *Aggress. Behav.* 8:163–168 (1982).]

Another animal model of human aggressive behaviors begins with the premise that every living species (human or animal) that can fight will fight, given the appropriate conditions. Thus, in this animal model system, an attack toward a territorial intruder or towards an unfamiliar group member; or a defense of one's young; or the competition for preferred food, mates, and niches of living; or a threat in the context of change in group formation and social standing—all are aggression provoking situations. These diverse types or forms of aggressive behaviors have collectively been termed "agonistic behaviors" in order to capture under one general heading the many different behavior elements typically encountered among these diverse conflict situations. [See for example: Scott, J. P., Aggression, University of Chicago Press, 1958; Scott, J. P., *Am. Zoologist* 6:683–701 (1966); Dixon, A. K. and H. P. Kaesermann, "Ethopharmacology of flight behavior," in *Ethopharmacology Of Agonistic Behavior In Animals And Humans,* Martinus Nijhoff, Dordrecht, 1987, pp. 46–70.]

A third kind of animal model system uses direct electrical or chemical stimulation of neural foci to evoke sequences of attack and defense behaviors as well as predatory attack in several animal species. In this model system, electrical neuronal activity is detected and often recorded; and the brain stimulation evoked aggressive or defensive behaviors exhibited by the animals is said to parallel in many respects the animal behavior seen in the wild or under natural conditions. [See for example: Siegel et. al., *Brain Res.* 93:473–484 (1975); Yamamoto et. al., *Jpn. J. Pharmacol.* 29:(Supp) 41P (1979); Conner e.t., al., *Physiol. Behav.* 5:1221–1224 (1970).]

In addition, as human aggressive behaviors became increasingly recognized as being of differing types and causes; and that a single type of human aggressive behavior may be pathological, or antisocial; the reported scientific investigations of neural mechanisms of action for aggression and therapeutic agent interaction have generated highly varied differences and sometimes even contradictions in information and knowledge. These reported experimental differences, empirical discrepancies, evidentiary inconsistencies, and conclusionary contradictions are often the consequence of intrinsic differences in the overall investigative strategy chosen for use. Traditionally, two different investigative strategies have been pursued. A first type (I) of research study uses drugs as tools for identifying and characterizing the neural mechanisms that might underlie a specific kind of aggressive behavior. This first type (I) assumes that the mechanism of drug action is well understood; and thus the experimental results are a direct reflection and consequence of specific drug interactions—a questionable premise. Alternatively, the second type (II) of investigative strategy employs specific aggressive acts as a means to screen for evaluating a novel compound or class of drugs; or to serve as markets for a specific neurotransmitter, a specific neurotransmitter activity, or a neurotransmitter receptor protein. The underlying premise and assumption of these second type (II) investigations is that the selected aggressive behavior and its neural basis are known, well understood, and adequately described in the literature.

Unfortunately, it is generally now appreciated that the in-vivo mechanisms for even the simplest aggressive act and behavior are very complex and incompletely understood. Any type of aggression and aggressive behavioral action must be carefully characterized and individually distinguished as to specific origin, type and nature. The scientific literature is replete with reviews and classification frameworks describing, separating, and distinguishing among the many forms of behavioral aggression. Merely representative of such publications are the following, the texts of which are each expressly incorporated by reference herein: Maxmen, J. S. and N. G. Ward, *Essential Psychopathology And Its Treatment,* Second edition, W. W. Norton & Co., 1995; *HANDBOOK OF PSYCHOPHARMACOLOGY* (Iversan et. al., editors), Vol. 19, 1987, Plenum Publishing Corp., Chap. 4, pp. 183–328; Drews, C., "The Concept And Definition Of Dominance In Animal Behavior", Behavior 125:286–313 (1993); Miczek, K. A. and P. Donat, "Brain 5-HT System And Inhibition Of Aggressive Behavior", in BEHAVIORAL PSYCHOPHARMACOLOGY OF 5-HT (Bevan, Cools & Archer, editors), 1989, Lawrence Erlbaum Associates, Chap. 10, pp. 117–144].

Equally important today in understanding properly the behavioral complexities of aggression behaviors and aggressive interactions is the now generally discredited theory and erroneous view that modifications of a single neurotransmitter might yield meaningful changes in aggressive behavior. It is important to note that at varying times in the history of this technological field, each of the known endogenous biogenic amines present in the brain and/or neural tissue was suspected of being the critical "code" or key to controlling and modifying aggressive behavior. Thus, in turn, the "aggressive monoamines" [Eichelman et. al., *Pharmacol. Blochem. Rev.* 1:121–123 (1973)], hypothalamic acetylcholine [Smith et. al., *Science* 167:900–901 (1970)], and serotonin [Valzelli. L. and S. Grattini, Adv. Pharmacol. 6B: 249–260 (1968)] each were offered and wrongly presented as being mediators in the control of all aggressive behavior. About 1970, the single neurotransmitter theory of control was expanded initially to a "neurochemical dualism" and then eventually increased to a theory of multitransmitter control of aggressive behaviors. [See for example: Reis, D. J., "The chemical coding of aggression in brain" in *Neurohumoral Coding Of Brain Function,* 1974, Plenum Press, pp. 125–150; Avis, H. H., *Psychol. Bull.* 81:47–63 (1974); Pradhan, S. N., "Aggression And Central Transmitters" in *International Review Of Neurobiology,* 1975, Academic Press, p. 213; Daruna, J. H., *Neurosci. Biobehav. Rev.* 2:101–113 (1978)]. Within these theories, just as a nerve cell membrane may either be excited or inhibited at the cellular level, aggressive behavior was wrongly believed to be under the excitatory and inhibitory control by functionally opposite neurotransmitters. The candidates for such behavioral excitation were initially thought to be norepinephrine and acetylcholine, which were later supplanted by dopamine and serotonin. This concept of exciting and inhibiting aggressive behavior by opponent neurotransmitters is seen today as overly simplistic and unable to account for the origins, range, and diversity of aggressive human behaviors as well as failing to explain or account for the behavioral complexities of aggressive interactions among members of the same species, much less between individuals of different species. [See for example: Miczek, K. A., "The Psychopharmacology of Aggression," in Handbook of Psychopharmacology, (Ivarsan et. al., editors), Plenum Pub. Co., Vol. 19, 1987, Chap. 4, pp. 183–328 and the references cited therein.]

With the complete discrediting of the "code" neurotransmitter theories for controlling all human aggression behaviors generally, the recent trends of research investigations and psychopharmacological experimentation in this field have begun to explore what might be the actual function of the various endogenous neurotransmitters and the true nature of their interactions in specific kinds of human aggressive behaviors, often using carefully selected animal models representative of a specific type of human aggression. These more recently published reports have typically followed one of two different investigative themes: Evaluations of active neurotransmitters and/or neurotransmitter metabolites in living human patients suffering from specific and well characterized forms of aggression; and purposeful challenges of neurotransmitters and/or their receptors within selected animal models putatively representative of a specific human aggressive behavior.

Exemplifying the investigations of neurotransmitters and their metabolites within human patient pools exhibiting a specified form of aggressive behaviors are the following publications: Serotonin in obsessions, compulsions and aggressive impulses of man [Insel et. al., *Ann. N.Y. Acad. Sci.* 487:574–582 (1987)]; biological correlates of suicidal risk and aggressive behavior traits in man [Linnoila, M. and M. Virkkunen, *J. Clin. Psychopharmacol.* 12:19S–20S (1992)]; central serotonin and impulsive aggression in man [Coccaro, E. F., *Brit. J. Pysch.* 155:52–62 (1989)]; serotonin, suicide, and aggression in man [Golden et. al., *J. Clin. Psych.* 52:61–69 (1991)]; relationships between central and peripheral serotonin indexes in depressed and suicidal psychiatric inpatients [Mann et. al., *Arch. Gen. Psychiatry* 49:442–446 (1992)]; the relationship of tryptophan, 5-HIAA, and IAA to sex, age, epilepsy and anticonvulsive drugs [Young et. al, *J. Neurol. Neurosurg. Psych,* 43:438–445 (1980)]; CSF neurochemistry in depressed, manic and schizophrenic human patients compared to human normal controls [Gurner et. al., *Am. J. Psych.* 141:1533–1540 (1984)]; suicidality and 5-HIAA concentration associated with the tryptophane hydroxylase gene in man [Nielsen et. al., *Arch. Gen Psychiatry* 51:34–38 (1994)]; personality profiles and state aggressiveness in Finnish alcoholic, violent offenders, fire setters, and healthy volunteers [Virkkunen et. al., *Arch. Gen Psychiatry* 51:28–33 (1994)]; serotonin correlates of suicidal and aggressive behaviors in man [Coccaro, E. F. and R. J. Kavoussi, *Neuropsychopharmacoloqy* 10:726S–727S (1994)]; and the role for central 5-HT receptor function in impulsive aggressive behavior in humans [Coccaro et. al., *Psychopharmacoloqy Bulletin* 26:393–405 (1990)].

In comparison, the investigations of neurotransmitters, their metabolites, and chemical challenges of these within controlled animal models representative of a specific human aggression behavior are merely represented by the following publications: reconciling the role of central serotonin neurons in human and animal behavior using rats [Soubrie, P., *The Behavior And Brain Sciences* 9:319–364 (1986)]; relationship between dominance hierarchy, cerebrospinal fluid levels of amine transmitter metabolites (5-HIAA and homovanillic acid) and plasma control in monkeys [Yodyingyuard et. al., *Neuroscience* 16:851–858 (1985)]; hormone-dependent aggression in male and female rats [Albert et. al., *Neurosci. Biobehav. Rev.* 16:177–192 (1992)]; the increase of serotonin but not dopamine metabolites in brain regions of subordinate rats in a colony [Blanchard et. al., *Brain Res.* 568:61–66 (1991)]; the reversal of testosterone-induced dominance by the serotonergic agonist quipazine between male rat pairs [Bonson, K. R. and J. C. Winter, *Pharmacology Biochemistry and Behavior* 42:809–81 3 (1992)]; effects of monoaminergic agonists on alcohol-induced increases in mouse aggression [Wagner et. al., *J. Stud. Alcohol, Supp.* 11:185–191 (1993); serotonergic control of anabolic steroid-induced aggression in rats [Bonson et. al., *Pharmacology Biochemistry and Behavior* 49:31 3–332 (1994)]; aggressive behavior in mice lacking 5-HT$_{1B}$ receptor [Saudou et. al., *Science* 265:1875–1878 (1994)]; serotonergic mechanisms promoting dominance aggression in adult male vervet monkeys [Raleigh et., al., *Brain research* 559:181–190 (1991)]; prolactin responses to fenfluramine challenge in adult male cynomolgus macaques [Botchin et. al., *Neuropsychopharmacology* 9:93–99 (1993)]; the role of brain serotonin neurons in dominance-subordination behavior among rats [Kotowski et. al., *Physiol. Behav.* 33:365–371 (1984)]; and inherent and environmental factors influencing serotonergic activity and behavior in monkeys [Kaplan et. al., *Neuropharmacology* 10:389S (1994 )].

The historical overview presented herein thus reveals that the various animal models have been and remain today a primary research investigative tool used for the betterment of humans and human problems as well as an aid to physicians and psychiatrists in the therapeutic treatment of human pathological behavioral disorders. However, even today there is much which is not yet understood about the actions of active psychopharmacological agents and their effects upon the various forms of human pathological behavior disorders. Equally important, as limited as the comprehension is today regarding the complexity of human psychopharmacological treatments for specific forms of human aggression behaviors, the quantum of knowledge and information directed to veterinary behavioral problems and a purposeful veterinary use of psychopharmacological agents for clinically modifying a varied range of animal aggressive behaviors is far more circumscribed and far less reliable. Accordingly, the generation and clinical demonstration of an effective veterinary psychopharmaceutical treatment method clinically to modify animal affective aggression behaviors in a household pet would be viewed as an unforeseen development, unusual benefit and marked advantage by practicing veterinarians.

SUMMARY OF THE INVENTION

The present invention is a veterinary method for clinically modifying the behavior of a household dog exhibiting a type of canine affective aggression. This veterinary behavioral modification method comprises steps of:
- administering to the household dog exhibiting a type of canine affective aggression behavior an effective amount of at least one selective serotonin reuptake inhibitor compound; and
- allowing sufficient time for said administered selective serotonin reuptake inhibitor compound to modify clinically the canine affective aggression behavior of the household dog.

BRIEF DESCRIPTION OF THE FIGURES

The present invention may be more easily and completely understood when taken in conjunction with the accompanying drawing in which:

FIG. 1 is a canine overt aggression score chart employed experimentally;

DETAILED DESCRIPTION OF THE METHODOLOGY

Figure 2:
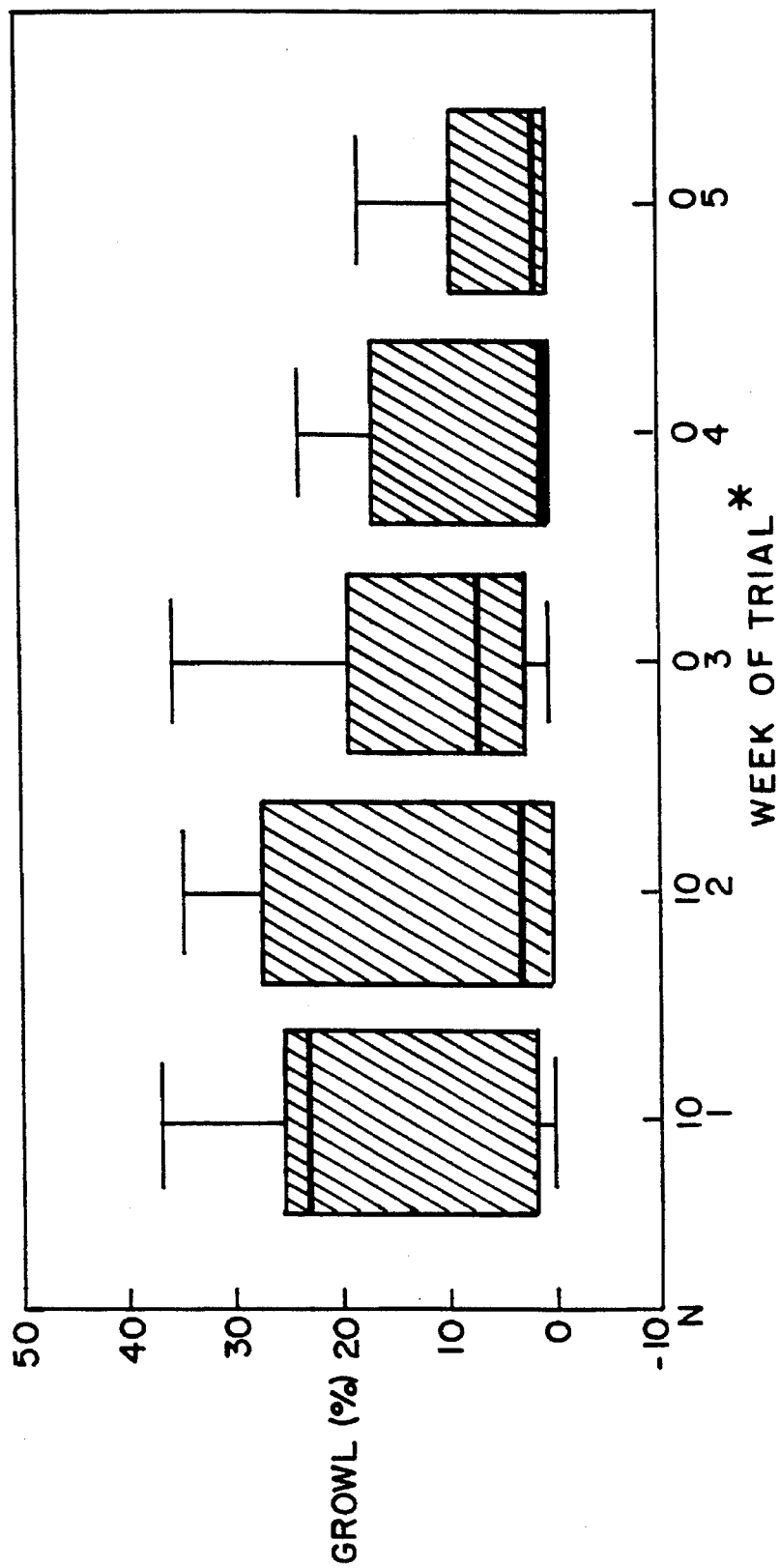
FIG. 2 is a graph illustrating a boxplot of growling behavior for dogs experimentally treated with fluoxetine as a function of treatment time.

The present invention is a clinical treatment method for modifying the observed behavior of a household dog which exhibits a characterized type of canine affective aggression behavior. The invention is thus a veterinary method pertinent to the observed behavior and purposeful treatment of animal behavior and is not merely a theoretical study of particular canine behaviors. To the contrary, as will be described in detail hereinafter, this veterinary method pertains to a readily identifiable category of dog behaviors termed "canine affective aggression behaviors"; and serves to modify clinically the undesired behavior of a household pet which exhibits a recognizable type of canine affective aggression. This veterinary behavior modification method provides multiple advantages and unexpected benefits which include the following:

1. The present veterinary method serves to modify the behavior of pet dogs suffering from canine affective aggression, the problem most commonly presented to practicing veterinarians. Because of the risks to human family members, the dog owners, as well as other persons, such forms of aggressive behavior are a source of intense emotional conflict for the dog owners and often have led to euthanasia of the pet. The present methodology provides a therapeutic alternative for modifying the undesirable and troublesome behavior of the pet dog; and will serve to diminish, if not entirely eliminate, the need for euthanasia as a means of resolution for these canine behaviors.

2. The present veterinary methodology can be utilized as a complete alternative to conventional techniques for modifying canine affective aggression behaviors in a household dog pet. Traditional approaches to behavior modification are limited and have employed conditioning techniques such as a withdrawal of attention, obedience training, the use of collars and leads, the avoidance of gratuitous petting or solicitousness, the use of fencing or other physical barriers, and calming exercises. The present invention may therefore be initially employed as an adjunctive therapy in combination with the conventionally employed conditioning techniques. In more severe instances and behaviors, a greater reliance and use of the methodology will provide major changes in dog behavior and a modification of decreasing aggression which is sustained for an indefinite period of time. Thus, the present invention may be used exclusively or in combination with conventional conditioning techniques in an adjunctive role which may itself be major or minor in duration and effect.

3. The present veterinary method may be employed over a wide range of time usages. Although a single dosage and treatment occasion may be partly effective in as little as a week's time, this is the least desirable mode of practicing the present invention. Instead, it is desirable that the method for modifying clinically the behavior be used in multiple dose and treatment occasions; be continued for 4–5 weeks duration once it has been initiated in order to obtain a major change of behavior in the household dog; and preferably will be extended for 2–6 months duration or even longer in order to obtain a permanent modification and change of behavior in the pet.

4. The veterinary methodology employs at least one selective serotonin reuptake inhibitor compound, of which a diverse and well characterized range of membership is presently licensed and commercially available. The methodology thus permits a choice of psychopharmacological agents whose specific properties and side effects may be individually matched to fit the age, general health, and personal characteristics of the household pet undergoing treatment. This range and variety of active agents thus provides both the practicing veterinarian and the human owners of the dog with some degree of latitude and flexibility in choosing the dose schedule and the preferred route of administration in order to obtain a modification and change in the behavior of the dog.

I. CLASSES AND TYPES OF VETERINARY AGGRESSION

A. Primary Classes Of Veterinary Aggression Behaviors.

Veterinary aggression generally has been classified and divided into two main categories: predatory aggressive behaviors and affective aggressive behaviors [Reis, D., *Neurosurg*, 18:471–502 (1971)]. Predatory aggression is innate, reflexive behavior triggered by moving prey (or perceived prey). This category of veterinary aggression involves minimal mood changes and is believed to be an automatic and preprogrammed form of behavior. Often, the term "instinctive behavior" is utilized as a reference to this class of veterinary aggression.

Affective aggression, on the other hand, is characterized by a marked mood change as well as by autonomic nervous system (sympathetic) activation which results in pupillary dilation and piloerection. Affective aggression can be offensive or defensive in form, depending on the inciting or initiating events. The animal's posture and the circumstances of his aggressive behavior often help distinguish between offensive and defensive behaviors.

Canine affective aggression behaviors are the problem most commonly presented to practicing veterinarians for treatment [Beaver, B. V., *Appl. Anim. Ethol.* 10:35–43 (1983)]. Due to the risks of injury to either the human family members who keep the dog as a household pet or to human strangers who are invited or incidentally intrude into the family household, affective aggression behaviors are a source of intensive emotional conflict for dog owners.

It is most important also to recognize and appreciate that canine affective aggression behavior—as a category of veterinary behavior—is considered to be a normal behavior for dogs generally; canine affective aggression behaviors are not usually pathological, diseased, or abnormal veterinary states or medical conditions. Equally important, canine affective aggression behaviors are radically different and completely unrelated to "affective aggression disorders in human psychiatry" which typically concern themselves with mental depression and mania as abnormal, irregular, and deviant human responses to the realities of every day life [See for example, *Current Medical Diagnosis & Treatment* 1986 (Krupp et. al., editors), Lange Medical Publications, pp. 670–673].

B. Recognized Types Of Canine Affective Aggression Behaviors.

Within the broad class encompassing canine affective aggression behaviors as a whole, a range of different types of representative behaviors are known and individually identifiable. Among them are those canine affective aggression behaviors which involve humans as the recipients of aggressive advances. This specific type of canine affective aggression behaviors is thus termed interspecies aggression—a term which describes interactions between two different species, e.g. dogs and humans. In contrast, affective aggression in which the dog's behavior is directed against a member of the same species is termed intraspecies aggression (i.e., dog versus dog interactions).

Most representative of the interspecies type of canine affective aggression behaviors are those described below.

Dominance-related aggression behavior:

Dominant-aggressive dogs exhibit growling, snarling or biting toward their owners and other familiar people. While each individual is unique, such dogs tend to act aggressive in the following circumstances:

1. When protecting food (dog food or human food), garbage, and certain objects (toys, stolen objects).
2. If disturbed while sleeping or resting, especially in socially significant areas such as furniture.
3. When a certain, closely bonded family member is approached or touched by other family members.
4. When they feel certain actions "threaten" this status. This can include certain postures such as bending over the dog, prolonged staring, punishment, pulling by the leash or collar, or even petting.

Dominance-related aggression may emerge in puppyhood, though dogs usually begin to exhibit serious aggression near the age of social maturity (1 to 3 years).

Territorial aggression behavior:

Territorial aggression is distinguished from dominance aggression by the target: while dominant-aggressive dogs direct threats to human family members, territorial dogs direct aggression towards human strangers. The natural tendency to sound an alarm when someone unfamiliar enters the home is exaggerated in some dogs. Territorial aggression is often a conditioned (learned) behavior, aggravated by long periods of unsupervised time within view of passersby. Aggressive barking, growling and biting threats can be exhibited in the home, yard, car or any area in which the dog has spent time (particularly with its family). Some dogs will threaten all who approach the owner while being walked on a lead. Such behavior is most pronounced in the socially mature dog (1 to 3 years), after which it tends to plateau. However, more severe aggression can be conditioned at any time. Males may be slightly more likely than females to exhibit territorial behavior. Any breed can be presented, though some are clearly predisposed (e.g. German Shepherd, Rottweiler, Kuvasz).

Fear-based aggression behavior:

Defensive or fear-based aggression can be displayed toward either family members or unfamiliar people. Owners may elicit a fear-related growl or bite when punishing their pets. Such behavior may be difficult to distinguish from dominance-related aggression without a detailed history of circumstances and postures assumed by the dog. Like dominance, fearfulness tends to be exhibited as a behavioral profile. Mildly affected dogs may threaten the source of their fear only in extreme circumstances, as during a veterinary visit; severely affected dogs may respond to more subtle threats. Such dogs often attempt to avoid threats, and will bite only when cornered or otherwise directly confronted. Fear-based aggression may be displayed by either sex, at any age. All breeds are affected; severely fearful dogs can be either genetically predisposed or environmentally conditioned (or both).

Aggression behavior directed toward children:

For understandable reasons, aggression behavior directed toward children in the home is particularly upsetting to dog owners. Dogs targeting children may be motivated by fear (e.g. due to lack of familiarity or memory of pain), dominance or predation. While adults may follow "rules" necessary for safety, toddlers and small children cannot be trusted to be consistent. Regardless of motivation for aggression, biting dogs should be leashed (attached to the owner) or actively supervised, muzzled or crated in the presence of small children. Aggressive behavior, which in some households may be regarded as mild, is potentially more dangerous in a home with children. Because of the natural transgressions of children, prevention of problems (as distinct from treatment) should be emphasized in such homes.

II. THE VETERINARY BEHAVIOR MODIFICATION METHODOLOGY

The methodology as a whole is intended to be practiced by veterinarians who are presented with a household pet by the human owners with the compliant that the dog has been either disobedient, overtly aggressive, or actually attacked or injured a human being. It is the veterinarian's first duty to ascertain and clinically diagnose whether the dog in question is exhibiting behavior which is properly characterized and described as a type of canine affective aggression behavior. The veterinarian will question the humans or owners of the pet; and may employ a behavioral score sheet chart similar to that illustrated by FIG. 1. It is clearly the practicing veterinarians responsibility to make the determination that the dog in question is exhibiting a type of canine affective aggression behavior; and also to identify whether that form is dominance-related aggression, territorial aggression, fear-based aggression, aggression directed toward children, or any other type properly included within affective aggression behaviors. The veterinarian may then choose one or more selective serotonin reuptake inhibitor compounds as the therapeutic active agent to be administered for modifying the dog's behavior.

A. Selective Serotonin Reuptake Inhibitor Compounds

A diverse range of pharmacologically active compounds which inhibit the serotonin transporter on serotonin neurons without inhibiting catecholamine uptake or antagonizing neurotransmitter receptors have been developed and approved for use. This class of compound has been termed "selective inhibitors of serotonin uptake"; comprises a range of compounds which are very different from one another in chemical structure; and share a common ability to inhibit the serotonin uptake carrier system [Fuller, R. W., *J. CLIN. Psychiatry* 53:36–45 (1992); Gram, L. F., N.E.J. Med. 331: 1354–1361 (1994); Lemberger et. al., *Clin. Neuropharmacol.* 8:299–317 (1985)]. Each of the suitable inhibitor compounds intended for use by the present methodology is thus well characterized as to chemical formulation, their high selectivity in their pharmocologic actions, and limited side-effects. Accordingly, all of these selective serotonin reuptake inhibitor compounds are deemed to be within the scope of the present invention and suitable for use within the present methodology.

Among the best known selective serotonin reuptake inhibitor compounds commercially available and licensed for use are those listed within Table 1 below. Among these fluoxetine or sertraline are the most preferred, having among the least side-effects and being well characterized as to their toxicity and biochemical activities. However, should the veterinarian decide that another inhibitor compound may be more desirable under specific treatment circumstances, any of the other compounds listed within Table 1 or any other selective serotonin reuptake inhibitor compound conventionally known in the scientific literature may be usefully employed with the present methodology as a complete and valuable choice.

any; and the severity of the canine affective aggression condition described by the dog's human family members.

Generally, oral administration ("per os") is favored; and the appropriate dosage can typically be admixed with the dog's food without major difficulty. In addition, the daily oral dosage will be from about 0.1–25.0 mg/kg of the chosen selective serotonin reuptake inhibitor compound, given once daily for some weeks' time or for 2–6 months, or even indefinitely.

If the preferred fluoxetine (or sertraline) is to be administered, the suggested dose schedule for treating a type of canine affective aggression behavior in dogs is desirably about 1.0 mg/kg by mouth once daily for a minimum time period of five weeks duration to affect a behavioral change and a longer two to four month treatment time for a maximum modification of behavior. Treatment may then be continued indefinitely or weaned-off (depending on the success of concurrent behavior modification).

Alternatively, should the desired route of administration be parenterally, the selective serotonin reuptake inhibitor

TABLE 1

Representative Selective Serotonin Reuptake Inhibitor Compounds

| Inhibitor Compound | Chemical Name | Conventional Human Dosage | References* |
|---|---|---|---|
| Fluoxetine | (±)-N-methyl-y-[4-(trifluoromethyl)phenoxy] benzenepropanamine | 20–80 mg/daily | U.S. Pat. No. 4,314,081; Stark et. al., J. Clin. Psychiatry 46 (Supp. 3):7 (1985); Wong et. al., Life Sci. 15:471 (1974). |
| Fluroxamine | 5-methoxy-1-[4-(trifluoromethyl)-phenyl]-1-pentanone O-(2-aminoethyl)oxime | 100–300 mg/daily | U.S. Pat. No. 4,085,225; Claasen et. al., Brit. J. Pharmacol. 60:505 (1977); Benfield, P. and A. Ward, Drugs 32:313 (1986). |
| Paroxetine | trans-(–)-3-[(1,3-Benzodioxol-5-yloxy)methyl]-4-(4-fluorophenyl)piperidine | 20–50 mg/daily | U.S. Pat. Nos. 3,912,743 and 4,007,196; Lassen, J. B., Eur. J. Pharmacol. 47:351 (1978); Hassan et. al., Brit. J. Clin. Pharmacol. 19:705 (1985). |
| Indalpine | 3-[2-(4-Piperidinyl)ethyl]-1H-indole | | U.S. Pat. No. 4,064,255; LeFur et. al., Life Sci. 23:59 (1978); Ashkenazi et. al., Brit. J. Pharmacol 79:915 (1983). |
| Citalopram | 1-[3-(Dimethylamino)propyl]-1-(4-fluorophenyl)-1-3-dihydro-5-isobenzofurancarbonitrile | | U.S. Pat. No. 4,136,193; Christensen et. al., Eur. J. Pharmacol. 41:53 (1977); Dufour et. al., Int. Clin. Psychopharmacol. 2:225 (1987). |
| Femoxetine | (3R-trans)-3-[(4-Methoxyphenoxy)-methyl]-1-methyl-4-phenylpiperidine | | U.S. Pat. No. 3,912,743; Lassen et. al., Psychopharmacologia 42:21 (1975); Dahl et. al., Acta Psychiatr. Scand. 66:9 (1982). |
| Zimeldine | (Z)-3-(4-Bromophenyl)-N,N-dimethyl-3-(3-pyridinyl)-2-propen-1-amine | | U.S. Pat. No. 3,928,369; Ross et. al., Life Sci. 19:205 (1976): Heel et. al., Drugs 24:169–206 (1982). |
| Sertraline | (1S-cis)-4-(3,4-Dichorophenyl)-1,2,-3,4-tetrahydro-N-methyl-1-naphthalenamine | 50–200 mg/daily | U.S. Pat. No. 4,536,518; Koe et. al., J. Pharmacol. Exp. Ther. 226:686 (1983); Saletu et. al., J. Neural Transm. 67:241 (1986). |
| Trazodone | 2-[3-[4-(3-chorophenyl)-1-piperazinyl]propyl]-1,2,4-triazolo[4,3-a]pyridin-3(2H)-one | | U.S. Pat. No. 3,381,009; Brogden et. al., Drugs 21:401–429 (1981); Gorecki, David R. Verbeeck, Analytical Profiles of Drug Substances, Vol. 16, Academic Press, 1986. |

*The Merck Index, 11th ed., Merck & Co., Inc., 1989; Drug Facts And Comparisons, 1995 Edition, A. Woltens Kluwer Co., pp. 1417–1430.

B. Pharmaceutical Formulations, Doses And Models Of Administration.

The selective serotonin reuptake inhibitor compound chosen for use with the veterinary treatment method herein can be administered in any appropriate carrier for oral or parenteral administration. The chosen compound can be any of those listed by Table; and be introduced in-vivo to the dog by any means or routing that substantively causes a clinical modification of canine affective aggression behavior in the subject. The dosage to be administered will vary and be dependent upon the age, general health, and weight of the recipient dog; the kind of concurrent medical treatment, if compound chosen for treatment will be prepared in sterile form; in multiple or single dose formats; and be dispersed in a fluid carrier such as sterile physiological saline or a 5% dextrose solution commonly used with injectables. All these dosages, schedules, and routes of administration are deemed to be within the scope of the present methodology.

C. Potential Complications, Contradictions, And General Considerations.

Potential complications include minor side effects of sedation, dry mouth, urinary retention, constipation, and lacrimation. In addition, there is the potential for seizures in a small percentage of patients. None has yet been recorded in dogs, but this side effect has been noted in 2–3% of human patients treated with serotonin reuptake inhibitors. A contraindication to the administration of a serotonin reuptake inhibitor to an animal would be historical or physical evidence of an existing seizure disorder. As with most other medications, paradoxical effects are sometimes observed early in treatment, e.g. in this case, tremors, restlessness, and inability to sleep. If these paradoxical effects are minor, they may be dealt with by reducing dosage of the medication, but if they become exceedingly troublesome, then the medication may have to be discontinued permanently or perhaps another serotonin reuptake inhibitor would have to be substituted. Paradoxical aggression is recorded in human patients, but this has not yet been observed in any veterinary patients.

EXPERIMENTS AND EMPIRICAL DATA

The experiments and in-vivo data provided hereinafter are a controlled setting showing the use of selective serotonin reuptake inhibitor compounds for clinical modification of canine affective aggression behaviors. While the empirical data presented is limited and employs fluoxetine for clinical modification of dominance-related aggression behavior in household dogs, these results and empirical data are direct evidence and probative facts illustrative of the general consequence of using selective serotonin reuptake inhibitor compounds clinically to treat each of the different types of canine affective aggression behaviors involving humans as an active participant described previously. For these reasons, the experiments and data provided are deemed to examplify and to represent the utility, benefits and value for the true scope of the present invention as defined.

Materials and Methods

Eleven dogs of mixed age and breed and of either sex were enrolled in a placebo controlled blind study to evaluate the efficacy of fluoxetine in the treatment of canine dominance-related aggression. One human owner failed to record data as requested so that data from ten dogs only were available for analysis. Each dog in the study was a clinical patient presented at the behavior clinic of Tufts University School of Veterinary Medicine. The human owners' primary complaint was that of aggression directed towards family members. Dominance-related aggression was confirmed by means of a canine overt aggression chart shown by FIG. 1. Aggression to human owners had to be evidenced in at least 5 listed circumstances in order for a diagnosis of dominance-related aggression to be confirmed. Owners of dogs showing dominance aggression were explained the details of this IACUC approved study and asked if they would be willing to enroll their dog in the study. If they agreed to participate they were asked to sign a formal consent form before proceeding.

The dogs were acquired serially and there was no attempt to select for any particular traits of owner or breed, sex or neuter status of the dogs. Owners enrolling their dogs in the study had to agree to medicate their dogs for five weeks, four weeks of active drug and one week a placebo, but were not informed which one of the five weeks was the placebo phase. They were required to record each instance of dominance-related aggression on a canine overt aggression chart on a daily basis. It was stressed that no behavior modification therapy or training should be conducted during the 5 week period to avoid confusing the results of flouxetine therapy. The total daily dose of fluoxetine was weighed to the nearest 0.1 /gram using an accurate chemical balance and was preloaded into #3 gelcaps. The placebo, administered during the first week of the study, consisted of an equal volume of saccharine in a #3 gelcap so that placebo and active drug were visually indistinguishable. A summary of the dogs enrolled in the study and the treatments given is provided by Table E 1 below.

TABLE E1

| Dog # | Breed | Gender | Age | Weight (kg) | Date Enrolled | Date Placebo Started | Date Fluoxetine Started | Capsule Weight (g) |
|---|---|---|---|---|---|---|---|---|
| 1 | Clumber Spaniel | neutered male | 6 years | 28.8 | 3/24/94 | 3/27/94 | 4/3/94 | 0.345 |
| 2 | Kerry Blue Tenier | neutered male | 2 years | 16.16 | 4/15/94 | 4/24/94 | 5/21/94 | 0.178 |
| 3 | Springer Spaniel | castrated male | 2 years | 22.5 | 6/1/94 | 6/12/94 | 7/10/94 | 0.248 |
| 4 | Cocker Spaniel | neutered female | 6 years | 13.5 | 6/24/94 | 7/10/94 | 7/17/94 | 0.149 |
| 5 | Cocker Spaniel | neutered male | 3 years | 11.4 | 7/4/94 | 7/17/94 | 8/13/94 | 0.125 |
| 6 | Toy Poodle | neutered male | 2 years | 5.3 | 8/28/94 | 9/11/94 | 10/8/94 | 0.059 |
| 7 | Dalmatian | neutered male | 9 months | 24.1 | 9/9/94 | 9/18/94 | 9/25/94 | 0.265 |
| 8 | Terrier Cross | neutered male | 3 years | 9.1 | 8/29/94 | 9/7/94 | 10/8/94 | 0.10 |
| 9 | Yellow Labrador Retriever | neutered male | 3 years | 27.5 | 9/11/94 | 9/24/94 | 9/29/94 | 0.303 |

A study monitor was available to answer any questions which arose during the study and owners were contacted on a weekly basis to actively solicit information pertaining to potential problems, to ensure that medication was being given on a regular basis, and to check that owners were having no problems completing the daily aggression score sheets. At the end of the five week study period, the score sheets were collected from participating owners and it was subsequently revealed to owners that the placebo phase was the first week of study.

Statistical Analysis

Each day, each of the dogs' response to a number of well-defined, specific situations (whether a growl, lip curl, snap or bite) was recorded on a canine overt aggression score chart identical to that shown by FIG. 1. "Not tried" and "no aggressive response" were also response options. Since not all situations were encountered by each dog each day, numbers of response occurrences were summed for each week and expressed as percentages of the number of situations encountered. These data are presented in the figures, as boxplots. In these plots, the heavy horizontal line represents the median occurrence, the shaded area includes those points which are between the 25th and the 75th percentile, and the bar extends to include all the data except outliers (which are indicated individually). Because of the nature of the data, the non-parametric Wilcoxon test for matched pairs used to analyze the data, with the first week's data (the control period) of each animal used as its own control.

Results

Figure 3:
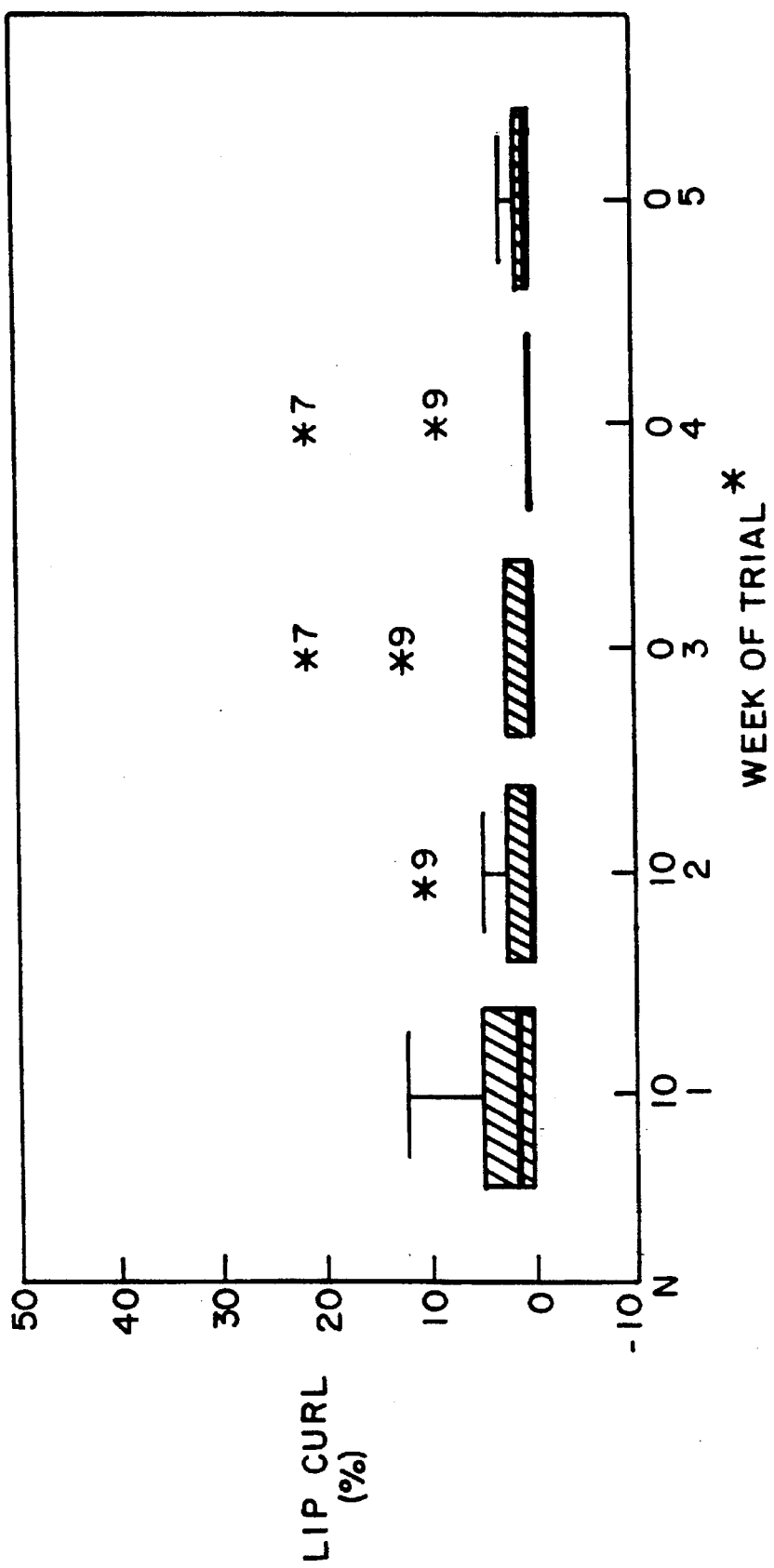
FIG. 3 is a graph illustrating a boxplot of lip curling behavior for dogs experimentally treated with fluoxetine as a function of treatment time.
Figure 4:
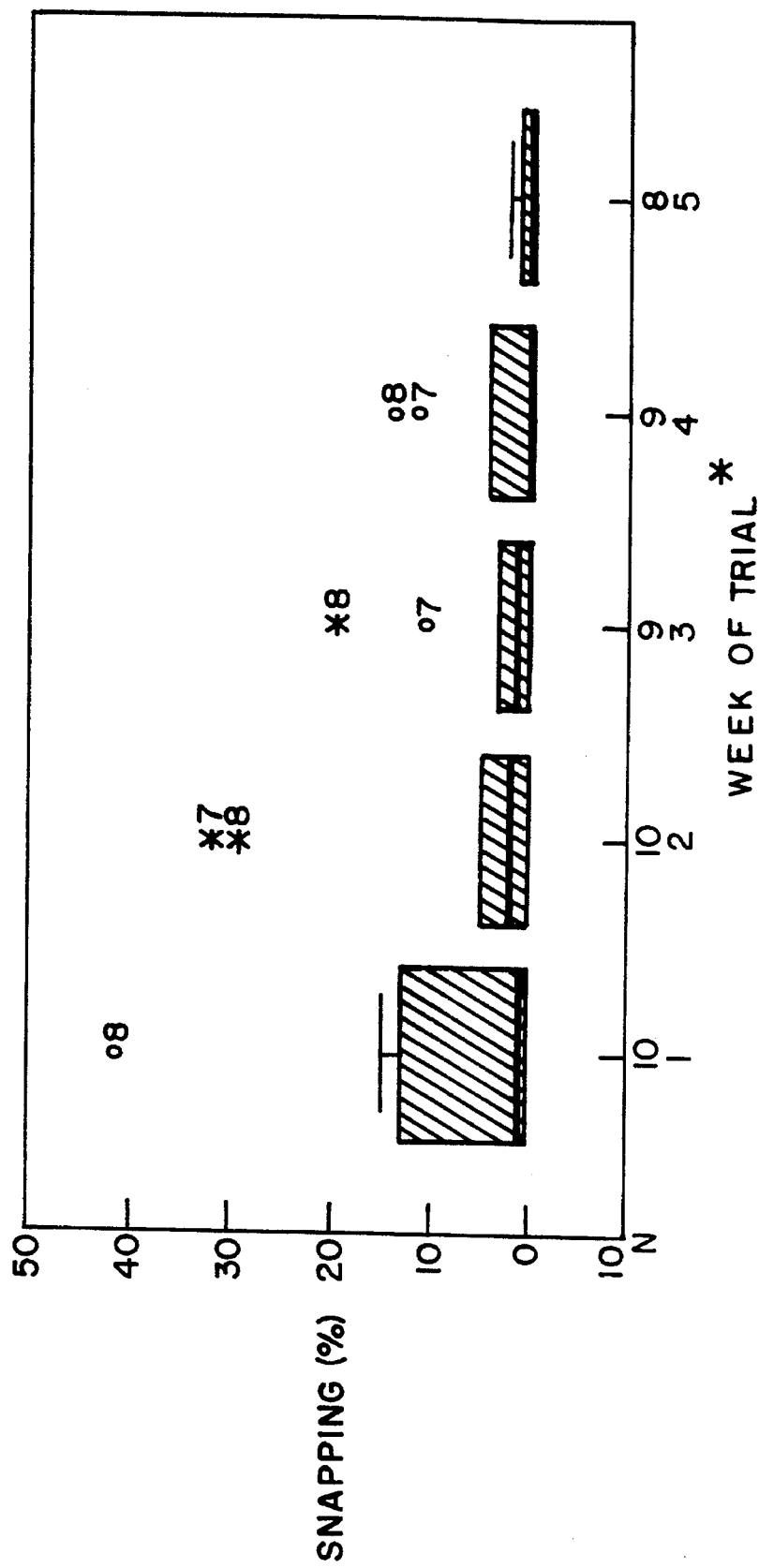
FIG. 4 is a graph illustrating a boxplot of snapping behavior for dogs experimentally treated with fluoxetine as a function of time.
Figure 5:
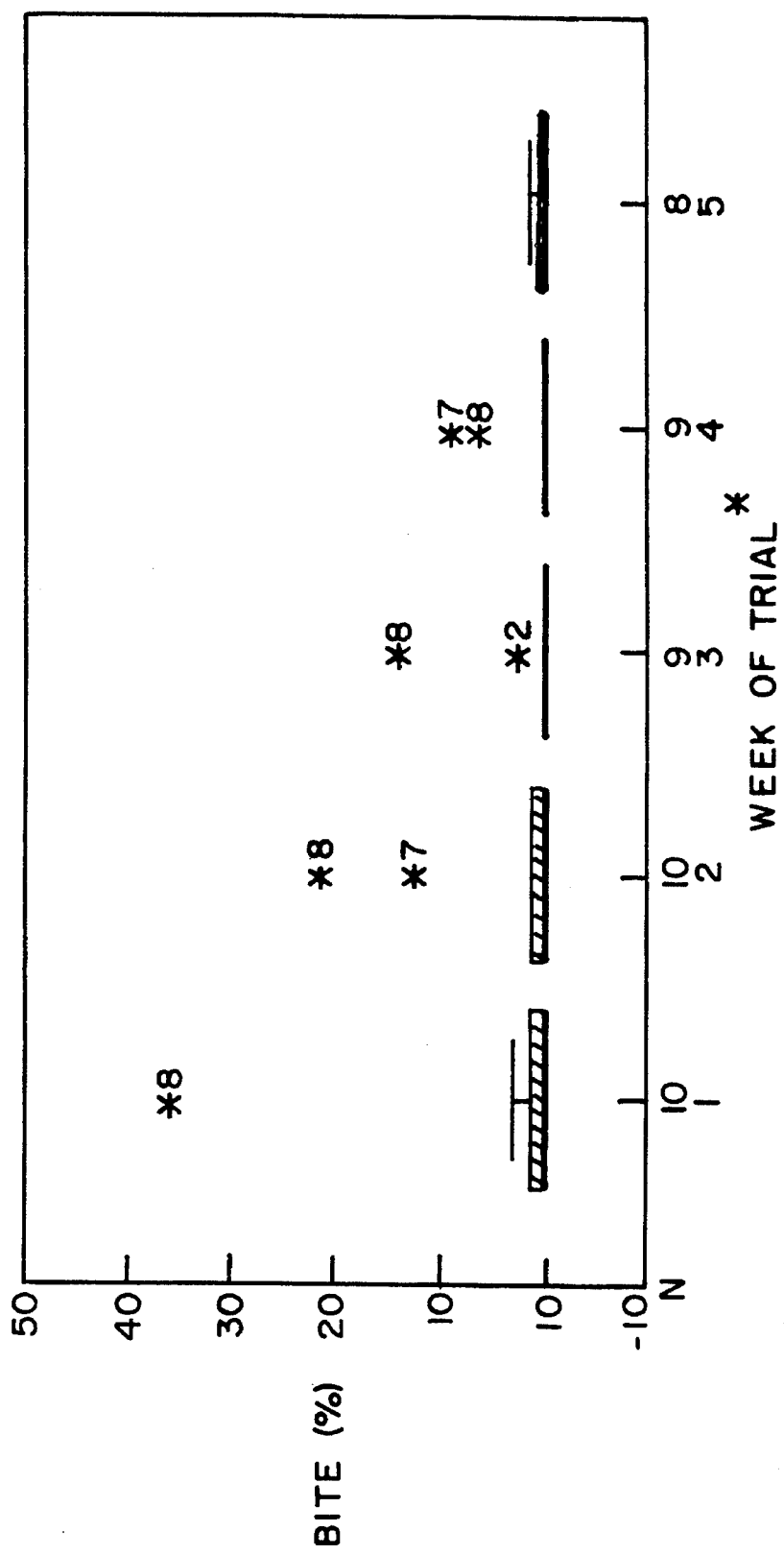
FIG. 5 is a graph illustrating a boxplot of biting behavior for dogs experimentally treated with fluoxetine as a function of time.
Figure 6:
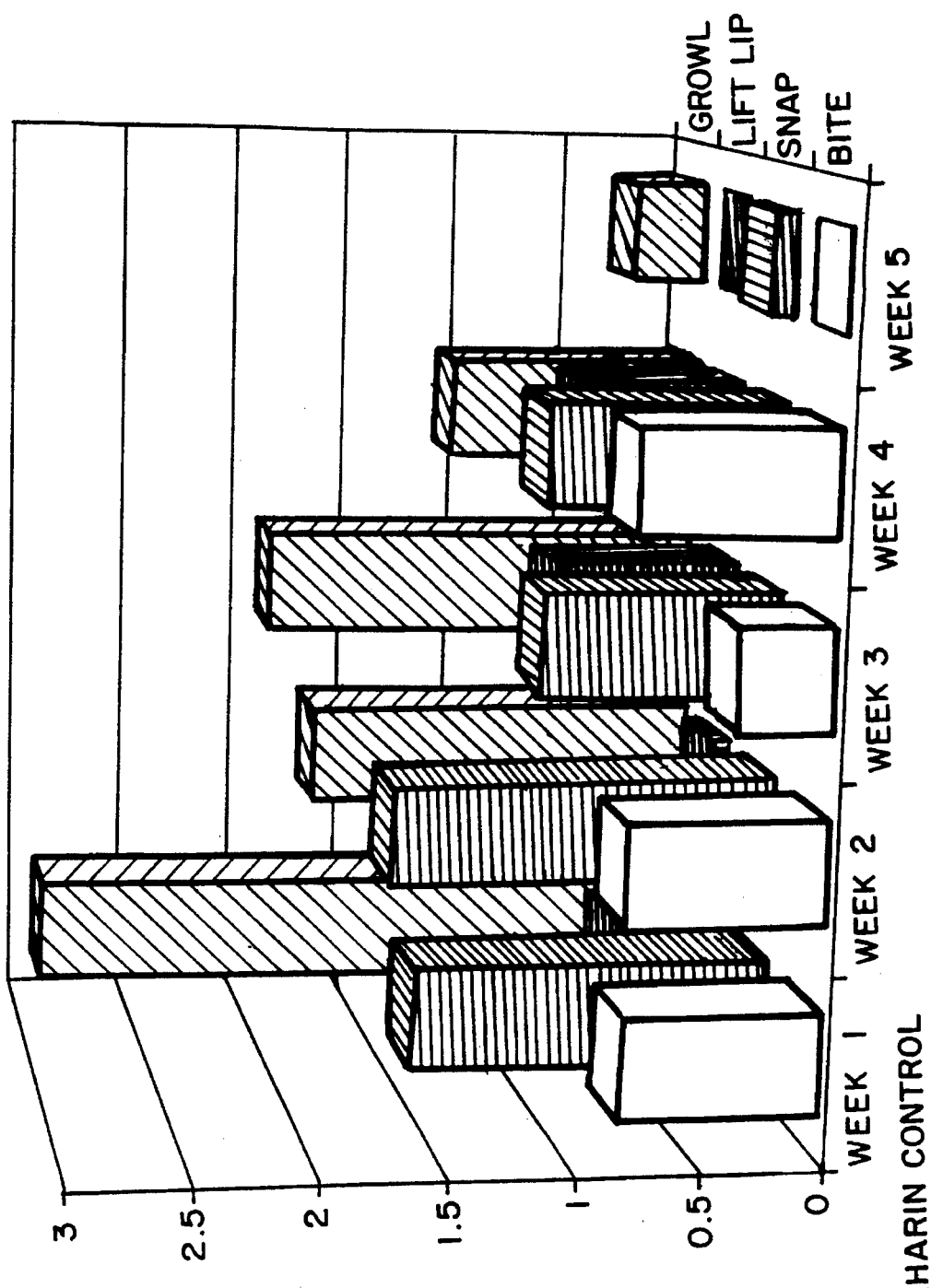
FIG. 6 is a graph summarizing the data of FIGS. 2, 3, 4, and 5 collectively.

Fluoxetine caused a significant reduction in owner-directed dominance aggression after four weeks of oral therapy. In particular, growling and a total aggression score showed a downward trend during the four week treatment period culminating in significant differences in both of these indices of aggression by the fourth week, as shown by FIG. 2. In most dogs, growling was the most common manifestation of aggression with other aggressive behavior (lip lift, snap, bite) occurring at too low a frequency for meaningful statistical analysis. These are illustrated by FIGS. 3, 4 and 5. In two dogs, however, snapping and biting were frequently elicited and, in one of these, (Dog #8) a dramatic decrease of this aggressive behavior was noticed over the experimental period. Seven of the ten owners felt that their dog was considerably less aggressive while under treatment with fluoxetine. One of these owners reported no aggressive incidence at all during the active drug phase of the study. Within this study, however, three owners were not able to perceive a substantial alteration in their dog's behavior, but in no case was aggression heightened. An overall summary of these results is provided by FIG. 6.

Conclusions

Fluoxetine, a representative member of the group of compounds termed selective serotonin reuptake inhibitors, is the most effective pharmacologic treatment ever described for the treatment of interspecific affective aggression in dogs. No drug has been described which is clinically satisfactory for the treatment of this otherwise relatively refractory and serious condition. Behavior programs on their own achieve a variable and limited degree of success and are both time consuming and necessitate a high level of owner compliance. Although the present study was purposefully conducted in the absence of any behavior modification therapy, it is envisaged that the combination of this therapy with the serotonin reuptake inhibitor treatment would provide even better results than drug treatment alone. Although the drug treatment does work on its own, as the results indicate, it is really envisaged that the pharmacologic treatment would provide more rapid and malleable control of affected dogs and thus increase owner compliance, motivation, and safety over and above that afforded by a behavior modification program alone. In general, it is regarded that this new therapy for canine affective aggression will revolutionize the treatment of this condition and reduce the current situation which leads to an overwhelming and unnecessary mortality (estimated ½–¾ million dogs per year are euthanatized because of aggression toward people).

This invention is not to be limited in form nor restricted in scope except by the claims appended hereto.

What I claim is:

1. A veterinary method for clinically modifying the behavior of a household dog exhibiting a recognized type of canine affective aggression behavior, said veterinary behavioral modification method comprising the steps of:

clinically determining that the household dog exhibits a recognized type of canine affective aggression behavior;

administering to the household dog exhibiting a recognized type of canine affective aggression behavior an effective amount of at least one selective serotonin reuptake inhibitor compound sufficient to cause a clinical modification of the canine affective aggression behavior in the household dog; and allowing sufficient time for said administered effective amount of selective serotonin reuptake inhibitor compound to modify clinically the canine affective aggression behavior of the household dog.

2. A veterinary method for clinically modifying the behavior of a household dog exhibiting a recognized type of canine affective aggression behavior, said veterinary behavioral modification method comprising the steps of:

clinically determining that the household doff exhibits a recognized type of canine affective aggression behavior;

administering to the household dog exhibiting a recognized type of canine affective aggression behavior a first effective amount of at least one selective serotonin reuptake inhibitor compound sufficient to cause a clinical modification of the canine affective aggression behavior in the household dog; and allowing sufficient time for said first administered effective amount of selective serotonin reuptake inhibitor compound to begin clinical modification of the canine affective aggression behavior of the household dog; and administering a second effective amount of said selective serotonin reuptake inhibitor compound to the household dog sufficient to cause a further clinical modification of the canine affective aggression behavior of the household dog.

3. The veterinary behavior modification method as recited in claim 1 or 2 wherein said recognized type of canine affective aggression behavior is an interspecies interaction behavior between a household dog and humans.

4. The veterinary behavior modification method as recited in claims 1 or 2 wherein said recognized type of canine affective aggression behavior is one selected from the group consisting of dominance-related aggression behaviors, territorial aggression behaviors, fear-based aggression behaviors, and aggression behavior directed towards children.

5. The veterinary behavior modification method as recited in claim 1 or 2 wherein said administered selective serotonin reuptake inhibitor is selected from the group consisting of fluoxetine, fluvoxamine, paroxetine, indalpine, citalopram, femoxetine, zimeldine, sertraline, and trazadone.

6. The veterinary behavior modification method as recited in claim 1 or 2 wherein said selective serotonin reuptake inhibitor is administered orally to the household dog.

7. The veterinary behavior modification method as recited in claim 1 or 2 wherein said selective serotonin reuptake inhibitor is administered parenterally to the household dog.

* * * * *